United States Patent [19]

Jongsma

[11] 4,379,026
[45] Apr. 5, 1983

[54] PROCESS FOR THE PURIFICATION OF BENZALDEHYDE

[75] Inventor: Cornelis Jongsma, Oirsbeek, Netherlands

[73] Assignee: Stamicarbon, B.V., Geleen, Netherlands

[21] Appl. No.: 341,108

[22] Filed: Jan. 20, 1982

Related U.S. Application Data

[63] Continuation-in-part of Ser. No. 125,661, Feb. 28, 1980, abandoned.

[30] Foreign Application Priority Data

Mar. 2, 1979 [NL] Netherlands ............................ 7901670

[51] Int. Cl.³ ............................................. B01D 3/34
[52] U.S. Cl. ........................................ 203/31; 203/32; 568/433; 568/438
[58] Field of Search ................... 568/438, 433; 203/28, 203/32, 31, 29

[56] References Cited

U.S. PATENT DOCUMENTS

1,935,914 11/1933 Olson .................................. 568/438
2,544,562 3/1951 Michael .............................. 568/438

*Primary Examiner*—Frank Sever

[57] ABSTRACT

A process for the purification in the presence of water of impure benzaldehyde by which a purified benzaldehyde is prepared which has improved color stability and improved olfactory characteristics. The process is comprised of the steps of treating the impure benzaldehyde simultaneously with water and a metal less noble than hydrogen followed by distillation.

20 Claims, No Drawings

PROCESS FOR THE PURIFICATION OF BENZALDEHYDE

The present application is a continuation-in-part of my copending application Ser. No. 125,661 filed Feb. 28, 1980 now abandoned.

The present invention is a new and novel process for the purification of benzaldehyde in the presence of water, and is in particular, a significant improvement in the purification in the presence of water of benzaldehyde prepared by the oxidation of toluene with a gas containing molecular oxygen.

BACKGROUND OF THE INVENTION

Benzaldehyde is an important starting material in various chemical syntheses including those relating to the synthesis of scents and flavors. In these applications, the benzaldehyde is often required to have a high degree of purity, but unfortunately crude benzaldehyde and especially benzaldehyde prepared by the oxidation of toluene with a gas containing molecular oxygen will contain certain impurities that are very difficult to remove. One very significant problem presented by these impurities is that it is particularly difficult to obtain a product from such crude benzaldehyde that will satisfy olfactory specifications. Furthermore, the presence of such impurities also causes a quite rapid discoloration of the benzaldehyde during storage. Such discoloration will occur even at very low concentrations of the impurities, such as a few p.p.m. by weight.

One suggested solution which appears in Japanese Patent Publication 24.467/74 is to purify the crude benzaldehyde by treating it with an aqueous solution of sodium hydroxide. However, this method of purification does not give satisfactory results as shown by the fact that benzaldehyde treated in this manner is still found to discolor quite rapidly.

One method which does give satisfactory results is that disclosed in U.S. patent application Ser. No. 952,609 filed on Oct. 18, 1978. The process disclosed in that application employs an oxidizing agent and distillation to accomplish the purification of impure benzaldehyde.

Still another method of purifying impure benzaldehyde is disclosed in a sister application of the present application filed on the same date in the U.S. Patent Office and which issued on Aug. 25, 1981 as U.S. Pat. No. 4,285,777. There the solution was found to be the treating of the impure benzaldehyde with hydrogen in the presence of a hydrogenation catalyst followed by a distillation step.

DESCRIPTION OF THE INVENTION

The present invention provides a process by which impure benzaldehyde in the presence of water may be purified. In accordance with the process of the present invention, purified benzaldehyde is obtained by treating the impure benzaldehyde simultaneously with water and with a metal less noble than hydrogen. The treated benzaldehyde is then distilled.

Prior to distillation, the phases formed during the purification may be separated and only the organic phase subject to the subsequent distillation step.

Metals which are suitable for use in the process of the present invention are metals of Groups IA, IIA, IIB, IIIB, IVA and VIII of the periodic table of elements, such as sodium potassium, iron, magnesium and calcium. Surprisingly, two metals which are particularly suitable for use in the present invention are aluminum and zinc. Normally, the amount of metal used ranges from about 0.1 mgat to 1000 mgat of metal per kg of benzaldehyde, but often the amount of metal used will be in the range of from about 1 to 200 mgat of metal per kg of benzaldehyde.

A suitable temperature range for the purification of benzaldehyde according to the process of the present invention is from about the freezing point of water under the reaction conditions, i.e., about 270 K. to about 500 K. Temperatures higher than about 500 K. may also be used. Particularly suitable are temperatures between about 280 and about 400 K. The duration of the treatment may vary between, for instance, about 0.1 and about 4 hours. The reaction pressure is not critical, but it should be such that the liquid phase is maintained. The pressure may be, for instance, between about 10 and 1000 kPa. A pressure approximately equal to the atmospheric pressure for instance, between about 50 and about 200 kPa, is preferable for practical reasons.

Suitable quantities of water for the purification of benzaldehyde are, for example, about 1 to about 1000 g per kg of benzaldehyde. Particularly suitable are quantities of between about 10 and about 150 g per kg of benzaldehyde.

Distillation of the treated benzaldehyde may be carried out at atmospheric or elevated pressure, but preferably at a reduced pressure, such as a pressure of between about 2 and 35 kPa.

In the process of the present invention, the loss of benzaldehyde is relatively small, usually in the range of about 1 to 5% by weight. Benzaldehyde having satisfactory olfactory characteristics is obtained even if the crude benzaldehyde had been prepared by oxidation of toluene.

To shorten the required treatment time and/or to lower the required treatment temperature, a base may be added to water. Suitable bases are water soluble bases, such as hydroxides and carbonates of alkali and alkaline earth metals, ammonia, or water soluble organic bases like amines. Particularly suitable are the hydroxides and carbonates of sodium and potassium, and calcium hydroxide. Quantities up to about 5000 mmoles of base per kg of benzaldehyde may be used and in particular quantities up to 500 mmoles per kg of benzaldehyde are very suitable. The quantity of base is calculated as the equivalent quantity of NaOH.

It is most surprising that crude benzaldehyde can be purified in this manner. It is well known that benzaldehyde will react with a hydroxide solution in a Canizarro reaction to form benzyl alcohol. See, for example, Roberts and Caserio, Modern Organic Chemistry, W. A. Benjamin, New York, Amsterdam, 1967, pp. 330, 331, 628. This makes the present invention all the more remarkable as it is now possible to purify benzaldehyde with a hydroxide solution and an ignoble metal without a substantial loss of benzaldhyde.

One suitable method for carrying out the process of the present invention is to pass the mixture of impure benzaldehyde and water to which a base may have been added over a bed containing solid metal particles. Particularly suited for this purpose is a bed containing zinc powder. This provides the additional advantage of not having to remove metal particles from the reaction mixture after treatment. A bed of this type also has the advantage of having an extremely long period of operation because of the very slow depletion of the metal present in the bed.

Another very suitable method for practicing the process of the present invention, which may be combined with the mode described above, is to treat the impure benzaldehyde with base free water and a metal less noble than hydrogen after which the resultant liquid phases are distilled without any separation of the phases. The advantage of this method is that the separation of the aqueous phase from the organic phase which is at times difficult can be omitted. If desired the metal particles present in the reaction mixture after treatment may be left in this mixture. If the organic and aqueous phases are left together for distillation, it is advantageous to use as little water as possible in order to reduce the amount of energy required during the distillation.

The invention will be elucidated further by means of the following non-restrictive examples and comparative experiment. The color value in degrees Hazen (°H) was determined by ASTM D 1209/62.

EXAMPLES

Example I

A sample of benzaldehyde, prepared by oxidation of toluene in the liquid phase by means of a gas containing molecular oxygen with the use of a homogeneous cobalt catalyst, was treated with 0.5% by wt. zinc powder and 10% by vol. water for 0.5 hour at 353 K. and atmospheric pressure. After removal of the zinc powder, the mixture was distilled in a sieve-tray column with 30 trays at a top pressure of 20 kPa and with a reflux ratio of 1:3. The zinc powder was consumed during the reaction at a rate of 325 mg per kg of impure benzaldehyde. The color value of the main fraction was below the detection limit of 5° H. This main fraction was divided into two portions. One portion was heated for 6 hours under a nitrogen atmosphere. The color value increased to 25° H. The other portion was stored for 30 days in a dark bottle under a nitrogen atmosphere. At the end of this period, the color value had risen to 15° H.

Example II

A sample of the same liquid crude benzaldehyde as used in Example I was treated with 0.9% by wt. zinc powder and 12 vol. % 3 N aqueous sodium hydroxide solution for 0.5 hour at 283 K. and atmospheric pressure. The zinc powder was consumed during the reaction at a rate of 650 mg per kg of impure benzaldehyde. After separation of the phases, the organic phase was distilled under the same conditions as in Example I. The color value of the main fraction was below the detection limit of 5° H. This main fraction was divided into two portions. One portion was heated for 6 hours under a nitrogen atmosphere. The color value increased to 15° H. The other portion was stored for 30 days in a dark bottle under a nitrogen atmosphere. At the end of this period, the color value had risen to 10° H.

Example III

A sample of the same liquid crude benzaldehyde as used in Example I was treated with 0.5% by wt. aluminium powder and 50% by vol. 3 N aqueous sodium hydroxide solution for 0.5 hour at 283 K. and atmospheric pressure. The aluminum powder was consumed during the reaction at a rate of 2.7 g per kg of impure benzaldehyde. After separation of the phases the organic phase was distilled under the same conditions as in Example I. The color value of the main fraction was below the detection limit of 5° H. This main fraction was divided into two portions. One portion was heated for 6 hours under a nitrogen atmosphere. The color value increased to 15° H. The other portion was stored for 30 days in a dark bottle under a nitrogen atmosphere. At the end of this period, the color value had risen to 10° H.

Comparative Experiment

A sample of the same liquid crude benzaldehyde as used in Example I was distilled without previous treatment under the same conditions as in Example I. The color value of the main fraction was 25° H. This main fraction was divided into two portions. One portion was heated under a nitrogen atmosphere. After 0.2 hour the color value of this portion had increased to over 100° H. The other portion was stored for 30 days in a dark bottle under a nitrogen atmosphere. At the end of this period, the color value had risen to 50° H.

What is claimed is:

1. Process for the purification in the presence of water of impure benzaldehyde including odiferous impurities comprising the steps of:
   (a) reacting said impure benzaldehyde simultaneously with water and at least one metal less noble than hydrogen in Groups IA, IIA, IIB, IIA, IVA, and VIII of the periodic table of elements at conditions of temperature and pressure sufficient to eliminate at least a substantial portion of said odiferous impurities and wherein at least a portion of said metal is consumed in the reaction, and
   (b) distilling said reacted benzaldehyde.

2. The process of claim 1, wherein the metal is zinc.

3. The process of claim 1, wherein the metal is aluminium.

4. The process of claim 1, wherein the amount of water used is in the range between about 1 gram and about 1000 grams per kg of benzaldehyde.

5. The process of claim 4, wherein the amount of water used is in the range between about 10 grams and about 150 grams per kg of benzaldehyde.

6. The process of claim 1, wherein the amount of metal used is in the range between about 01. mgat and about 1000 mgat per kg of benzaldehyde.

7. The process of claim 6, wherein the amount of metal used is in the range between about 1 mgat and about 200 mgat per kg of benzaldeyde.

8. The process of claim 1, wherein the treatment of step (a) is carried out at a temperature in the range between about the freezing point of the water under the reaction conditions and about 500 K.

9. The process of claim 1, wherein the treatment of step (a) is carried out at a temperature in the range between about 280 K. and about 400 K.

10. The process of claim 1, wherein the time of the treatment of step (a) is in the range between about 0.1 hours and about 4 hours.

11. The process of claim 1, wherein a base is added to the water.

12. The process of claim 12, wherein a maximum of about 5000 mmoles of base is added per kg of benzaldehyde.

13. The process of claim 13, wherein a maximum of 500 mmoles of base is added per kg of benzaldehyde.

14. The process of claim 12, wherein the base is selected from the group consisting of a hydroxide of sodium, a hydroxide of potassium, a hydroxide of calcium, or mixtures thereof.

15. The process of claim 11, wherein the base is selected from the group consisting of a carbonate of sodium, a carbonate of potassium or mixtures thereof.

16. The process of claim 1, wherein the impure benzaldehyde was obtained by the oxidation of toluene with a gas containing molecular oxygen.

17. Process for the purification in the presence of water of impure benzaldehyde including odiferous impurities comprising the steps of:
   (a) admixing said impure benzaldehyde and said water,
   (b) passing said admixture of step (a) over a bed containing solid particles of at least one metal less noble than hydrogen in Groups IA, IIA, IIB, IIIA, IVA, and VIII of the periodic table of elements to purify said impure benzaldehyde, wherein said admixture and said bed are maintained at conditions of temperature and pressure sufficient to eliminate at least a substantial portion of said impurities and at least a portion of said metal in said bed is consumed, and
   (c) distilling said purified benzaldehyde.

18. The process of claim 17, wherein a base is added to the mixture of impure benzaldehyde and water.

19. The process of claim 17, wherein the bed contains zinc powder.

20. Process for the purification in the presence of water of impure benzaldehyde including odiferous impurities comprising the steps of,
   (a) reacting said impure benzaldehyde simultaneously with a base free water and at least one metal less noble than hydrogen in Groups IA, IIA, IIB, IIIA, IVA, and VIII of the periodic table of elements at conditions of temperature and pressure sufficient to eliminate at least a substantial portion of said odiferous impurities and wherein at least a portion of said metal is consumed in the reaction, and,
   (b) distilling said reaction mixture of step (a) without previous separation of liquid phases.

* * * * *